US012766270B2

(12) United States Patent
Evjensvold et al.

(10) Patent No.: US 12,766,270 B2
(45) Date of Patent: Oct. 20, 2026

(54) INJECTION DEVICE WITH MULTIPLE CANNULAS

(71) Applicant: DMC Innovation AS, Førde (NO)

(72) Inventors: Laila Rigmor Evjensvold, Forde (NO); Jens Ola Evjensvold, Forde (NO); Trine Evjensvold, Oslo (NO); Truls Evjensvold, Forde (NO)

(73) Assignee: DMC Innovation AS, Forde (NO)

( * ) Notice: Subject to any disclaimer, the term of this patent is extended or adjusted under 35 U.S.C. 154(b) by 966 days.

(21) Appl. No.: 17/923,919

(22) PCT Filed: May 11, 2021

(86) PCT No.: PCT/EP2021/062485

§ 371 (c)(1),
(2) Date: Nov. 8, 2022

(87) PCT Pub. No.: WO2021/228856

PCT Pub. Date: Nov. 18, 2021

(65) Prior Publication Data

US 2023/0173193 A1 Jun. 8, 2023

(30) Foreign Application Priority Data

May 11, 2020 (NO) .................................... 20200546

(51) Int. Cl.
*A61M 5/32* (2006.01)
*A61M 5/20* (2006.01)
(Continued)

(52) U.S. Cl.
CPC ...... *A61M 5/3298* (2013.01); *A61M 5/31513* (2013.01); *A61M 5/3295* (2013.01);
(Continued)

(58) Field of Classification Search
CPC .............. A61M 5/3298; A61M 5/3297; A61M 5/3295; A61M 37/0015;
(Continued)

(56) References Cited

U.S. PATENT DOCUMENTS 2,821,195 A * 1/1958 Mclintock ................ A61D 7/00 604/184
4,403,989 A * 9/1983 Christensen .......... A61M 5/204 604/137
(Continued)

FOREIGN PATENT DOCUMENTS

EP 3085410 10/2016
EP 3639873 4/2020
(Continued)

OTHER PUBLICATIONS

IPRP in PCT/EP2021/062485.
ISR and WOISA in PCT/EP2021/062485.
Norwegian Search report in applicaion No. 20200546.

*Primary Examiner* — Courtney D Heinle
*Assistant Examiner* — Wesley Le Fisher
(74) *Attorney, Agent, or Firm* — Troutman Pepper Locke LLP; Ryan A. Schneider; Nicholas H. Doss

(57) ABSTRACT

The present invention concerns an injection device for delivering a substance to the skin of a subject. The injection device is suitable for precise and even distribution of the substance to the skin and minimizing waste of injectable substance. The injection device comprises multiple cannulas, is connectable to standard syringes and particularly useful in dermatological treatments.

14 Claims, 13 Drawing Sheets

(51) Int. Cl.
*A61M 5/315* (2006.01)
*A61M 37/00* (2006.01)

(52) U.S. Cl.
CPC ........... *A61M 5/204* (2013.01); *A61M 5/3297* (2013.01); *A61M 37/0015* (2013.01)

(58) Field of Classification Search
CPC .... A61M 2037/0023; A61M 2037/003; A61M 2037/0038; A61M 2037/0046; A61M 2037/0053; A61M 2037/0061; A61M 5/204
See application file for complete search history.

(56) References Cited

U.S. PATENT DOCUMENTS

| | | | | | |
|---|---|---|---|---|---|
| 6,537,242 | B1 * | 3/2003 | Palmer | A61M 37/0015 600/583 |
| 6,623,457 | B1 * | 9/2003 | Rosenberg | A61B 17/205 604/272 |
| 6,716,187 | B1 * | 4/2004 | Jorgensen | A61M 1/029 604/407 |
| 7,556,615 | B2 * | 7/2009 | Pettis | A61M 5/3298 604/117 |
| 9,457,183 | B2 * | 10/2016 | Sallberg | A61N 1/306 |
| 10,238,812 | B2 * | 3/2019 | Ignon | A61B 17/545 |
| 10,589,076 | B2 * | 3/2020 | Sumida | A61M 5/425 |
| 10,814,116 | B2 * | 10/2020 | Sumida | A61M 5/3293 |
| 11,096,822 | B2 * | 8/2021 | Yamamoto | A61M 5/204 |
| 12,318,565 | B2 * | 6/2025 | Park | A61M 37/0015 |
| 2003/0050602 | A1 | 3/2003 | Pettis et al. | |
| 2003/0208167 | A1 * | 11/2003 | Prausnitz | A61M 37/0015 606/186 |
| 2013/0102954 | A1 | 4/2013 | Choi | |
| 2020/0188610 | A1 * | 6/2020 | Fretta | A61M 5/3293 |
| 2021/0353879 | A1 * | 11/2021 | Fugo | A61M 5/347 |

FOREIGN PATENT DOCUMENTS

| | | | | |
|---|---|---|---|---|
| IE | 930274 | A1 * | 10/1994 | A61M 5/425 |
| WO | WO2014/189161 | | 11/2014 | |
| WO | WO2016/053617 | | 4/2016 | |

* cited by examiner

INJECTION DEVICE WITH MULTIPLE CANNULAS

TECHNICAL FIELD

The present invention relates to an injection device for delivering a substance to the skin of a subject. The injection device is suitable for precise and even distribution of the substance to the skin and minimizing waste of injectable substance.

BACKGROUND AND PRIOR ART

Treatments for cosmetic enhancement including dermatology are used to restore or improve the shape and looks of the human skin. Over the years, healthcare professionals have developed numerous treatments including deep cutaneous and subcutaneous injection. Commonly known subcutaneous injection include filler injections and botulinum toxin injections. Sub-dermal injections are regarded as minimally invasive procedures for changing the aesthetics of the human skin. Common areas where the subcutaneous injection material is injected are the areas on the face, neck, hands, breast and buttocks, resulting in a change in their contours, resulting in a restored, younger-looking appearance.

Commercially available injectable types of substances include deoxycholic acid, hyaluronic acid, botulinum toxin, lidocaine, saline, hyaluronic acid filler, (E.g., calcium hydroxyapatite, poly-1-lactic acid, polyglycolic acid), collagen wrinkle filler, bovine collagen-containing polymethyl methacrylate, autogenous wrinkle filler, but are not limited thereto.

Hyaluronic acid is a common ingredient in skin care products. Hyaluronic acid is a normal ingredient in the intercellular space in human skin and is used as a dermal filler in cosmetic surgery. It is typically injected using a classic sharp, thin hypodermic needle, also called a microcannula.

A common method for administering a substance to the skin of a human subject is to use a device for injection. Typically, a syringe with a cannula is used. For cosmetic treatment this practice may not be well suited because a large number of injections are usually given in one treatment. It is also often critical for obtaining a good result that the substance to be injected is administered with an even distribution both with regards to distance between the injections and the depth of the injections in the area of skin that is treated. When using conventional syringe and cannula equipment such treatments are laboursome and demands great precision, concentration and patience for producing good results.

Some efforts have been made to provide a device for improving the administration of substances to the skin.

US2003/0208167 A1 discloses a microneedle device for administering a substance across or into the skin. The device includes a substrate with a reservoir which is in connection with a plurality of microneedles suitable for injection into the skin. The microneedles may have different shapes and lengths and the device is suitable for controlling the depth of injections by pushing the substrate onto the skin of a patient. There is no mention on how to evenly distribute the injections.

US20180264204 describes a needle injection array which comprises a fluid manifold configured to direct fluid from a syringe to arrive at the tip of the needles simultaneously. The needle injection array disclosed may be configured to secure a equal dose of fluid volume through the needles to an injection site.

Other commercial products are on the market. Restylane Skinbooster comprises hyaluronic acid in a syringe with a single cannula which are 1.2-1.3 mm long and has a diameter of 27-30 G. The product is for administering the hyaluronic acid to a skin area through micro-injections. When the device is used hand-held, it is up to the practitioner to set the depth of injection and the distance between them.

A device with the trade name “Mesogun” can be used with a skinbooster injection device. It is possible to fix the depth of injection to a predetermined depth. “Mesogun” is moved manually and it is difficult to obtain standardized distance between injections.

A device called “DermaPen” is also available on the market. This device has 9-12 needles that are not hollow cannulas. The substance to be administered is applied to the skin surface of a subject before the skin is perforated by the “DermaPen”. This result in doses that are hard to predict and the cosmetic effect on the skin is somewhat unpredictable.

The devices mentioned above do not provide convenient means for administering a substance to the skin of a subject in a uniform an even manner.

Furthermore, they let expensive substance for injection to go to waste after use, because rest volumes of injection fluid may be left behind when cannula arrays are used.

It is therefore an object of the present invention to provide an injection device suitable for use in skin treatment that is configured for providing doses of a substance to the skin, wherein the doses are evenly distributed in the skin area that is to be treated.

It is also an object of the present invention to provide a device suitable for minimizing the waste of the substance to be administered.

Finally, it is an object of the present invention to provide a method for even administration to an area of skin.

SUMMARY OF THE INVENTION

The present invention is set forth and characterized in the main claims, while the dependent claims describe other characteristics of the invention.

In one embodiment the invention concerns an injection cannula array device comprising a distribution chamber defined by a base end comprising a plurality of apertures for fluid communication from the distribution chamber to the outside, side walls connected to the base end, and a top end comprising an aperture for fluid communication from the distribution chamber to the outside, wherein said top end is connected to a fluid conduit for fluid communication through the aperture, and wherein the fluid conduit comprises a fluid conduit connector on the distal end from the distribution chamber, the fluid conduit connector suitable for connecting to a syringe, wherein the device further comprises; a plurality of cannulas, wherein each cannula is arranged for fluid communication with the respective plurality of apertures, and wherein each cannula extends from the respective aperture to a cannula tip distal from the base end outside the distribution chamber.

In a second embodiment the invention concerns an injection cannula array device comprising a distribution chamber defined by a base end comprising a plurality of apertures for fluid communication from the distribution chamber to the outside, side walls connected to the base end, and a top end comprising an aperture for fluid communication from the distribution chamber to the outside, wherein said top end is connected to a fluid conduit for fluid communication through the aperture, and wherein the fluid conduit comprises a fluid conduit connector on the distal end from the distribution chamber, the fluid conduit connector suitable for connecting to a syringe, wherein the device further comprises; a plurality of cannulas, wherein each cannula is arranged for fluid communication with the respective plurality of apertures, and wherein each cannula extends from the respective aperture to a cannula tip distal from the base end outside the distribution chamber, wherein the base end comprises a skirt extending from the edge of the base end at least a part of the length of the plurality of cannulas, wherein the skirt is suitable for leaving a distinct guiding mark on a skin surface after the skirt has been pressed against said skin surface.

The fluid conduit connector may be of the "Luer lock"-type, a conical connecter or other connector means well known to the skilled person.

In one aspect the invention concerns the injection cannula array device wherein the skirt extends between 5-90%, 10-80%, 10-70%, 10-60%, 20-50% or 30-50% of the length of the plurality of cannulas.

In one aspect the invention concerns the injection cannula array device according to any of the preceding claims, wherein the plurality of cannulas are arranged in rows, with a distance D between each of the plurality of cannulas, and wherein there is a row of said plurality of cannulas adjacent to the side skirt.

In one aspect of the invention the plurality of cannulas is arranged in a triangular pattern.

In one aspect of the invention the distribution chamber has a triangular shape.

In one aspect of the invention the distribution chamber has an equilateral triangular shape.

In one aspect the invention relates to the injection cannula array device wherein the distance from each cannula located adjacent to the skirt to the outer edge of said skirt is between ½ D×Cos 25°-½ D×Cos 35°, or between ½ D×Cos 29°-½ D×Cos 31° or ½ D×Cos 30°, when measured at angle perpendicular to the skirt.

In another aspect the invention relates to the injection cannula array device, wherein the distribution chamber has an inner shape of an equilateral triangle in the plane of the base end.

In one aspect the invention concerns the injection cannula array device, wherein the outer walls of the skirt comprises 5 surfaces, wherein said 5 surfaces is comprised of 2 connected long surfaces, each said surfaces connected to 2 respective corner surfaces at an end distal to the connection between the two long surfaces, and 1 short surface connected at each end to each respective corner surfaces, wherein the short surface is longer than the corner surfaces, and the long surfaces is longer than the short surface.

In one aspect the corner surface is ½ D long.

In one particular aspect the invention concerns the injection cannula array device, comprising a piston arranged slidingly within the distribution chamber, wherein the piston is arranged sealingly to the side walls, and the piston comprises an aperture for fluid communication from the distribution chamber through the fluid conduit, wherein the piston is configured with a start position (SP) at the top end and an end position (EP) at the base end, and wherein the piston is connected to the fluid conduit and configured to travel from the start position (SP) towards the end position (EP) when a predetermined force (N) is applied to the fluid conduit in the direction of the base end.

The skilled person understands that this aspect will work with either the first or the second embodiment of the invention, ie. with or without the base end being configured with a skirt for leaving a guiding mark on the skin surface.

In one aspect of the invention the piston has a triangular shape.

In one aspect of the invention the piston has an equilateral triangular shape.

In one aspect the invention relates to the injection cannula array device, wherein the side walls comprises a stop list protruding from the side walls proximal to the top end, into the distribution chamber, wherein the stop list is configured to engage with the piston, at the start position (SP), thereby hindering travel of the piston out of the distribution chamber.

In another aspect the invention relates to the injection cannula array device, wherein the top end comprises a top lid, wherein the top lid is arranged for covering the side walls and the piston, wherein the top lid comprises a top lid aperture for enclosing the fluid conduit and wherein the top lid is configured to be separated into at least two parts along a line traversing the top lid aperture.

In one aspect the invention relates to the injection cannula array device, wherein the top lid is configured to be separated into 3 parts.

In another aspect of the invention the top end comprises guiding pins for guiding the stop ring into the distribution chamber.

In one aspect the invention relates to the injection cannula array device, wherein the fluid conduit comprises a stop ring protruding from the outside of the fluid conduit, wherein the stop ring is arranged to engage the top lid, thereby preventing movement of the fluid conduit and securing the piston in the start position (SP) when the top lid is covering the side walls and the piston.

In yet another aspect the invention concerns the injection cannula array device, wherein the stop ring has a diameter suitable for a tight fit with the side walls when the piston travel from the start position (SP) towards the end position (EP), and wherein the stop list is configured with recesses for allowing the stop ring to pass by and into the distribution chamber.

In one aspect the invention concerns the injection cannula array, wherein the distribution chamber comprises a ventilating opening for evacuating air from the distribution chamber prior to injecting a patient. The ventilating opening is preferably located the corner of the distribution chamber where the two long surfaces are connected. The ventilating opening may be closable with a hatch or a lid or other closing means forming a water and air tight seal. The ventilating opening may in one configuration comprise a one way valve for evacuating air from the distribution chamber.

In one embodiment the present invention relates to a method for obtaining even distribution of an injection fluid by use of the injection cannula array device, comprising the steps A. connecting the injection cannula array device to a syringe comprising injection fluid B. inserting the needles into the skin of a patient and contacting the skin of a patient with the skirt by pressing the device against the skin of the patient with sufficient force for the skirt to leave a temporary line in the shape of the skirt on the skin surface of the patient, C. delivering a predetermined volume of injection fluid from the syringe, D. removing the injection cannula array device, E. spotting the temporary line in the skin surface of the patient, F. moving the injection cannula array device and aligning an outer surface of the skirt to the temporary line on the skin surface of the patient, G. optionally repeating step A.

The skilled person acknowledges that a practitioner can exchange an used or empty syringe for new one as many times as it is needed to complete a treatment of a predetermined area of skin.

In a final aspect the invention relates to the method by use of the injection cannula array device, wherein the method further comprises the steps of H. removing the top lid I. applying a force to the fluid conduit for pushing the piston towards the base end, thereby emptying the distribution chamber.

Definitions

"Cannula" as used herein is to be understood as a hollow needle for use in medical procedures such as injections and infusions.

"Array" is to be understood as an arrangement or pattern of cannulas in an apparatus or device.

"Distribution chamber" as used herein is to describe a hollow space within the device suitable for distributing an injection fluid to a plurality of cannulas.

"Substance for injection" and "injection fluid" is used herein as equivalent and refers to a fluid that is suitable for injection in a human or animal with an injection device.

"Fluidly connected" or "in fluid communication" means that the connection allows gas, air, steam and liquid fluid to enter from one component to another component of the device.

DETAILED DESCRIPTION OF THE INVENTION

In the following, specific embodiments of the invention will be described in more detail with reference to the drawings. However, the invention is not limited to the embodiments and illustrations contained herein. It is specifically intended that the invention includes modified forms of the embodiments, including portions of the embodiments and combinations of elements of different embodiments. It should be appreciated that in the development of any actual implementation, as in any engineering or design project, specific decisions must be made to achieve the developer's specific goals, such as compliance with system and/or business-related constraints. Moreover, it should be appreciated that such a development effort might be complex and time consuming, but would nevertheless be a routine undertaking of design, fabrication and manufacture for the skilled person having the benefit of this disclosure.

FIGS. 1-5 shows an embodiment of an injection device 100 that is suitable for fluid connection to a syringe 151. The injection device comprises a distribution chamber 114 and a plurality of cannulas arranged in a triangular shape. The injection device 100 is suitable for administering an injection fluid 150 evenly and uniformly to an area of skin by providing triangular shaped patterns of injections on a subject as shown in FIGS. 3-5.

Figure 6A:
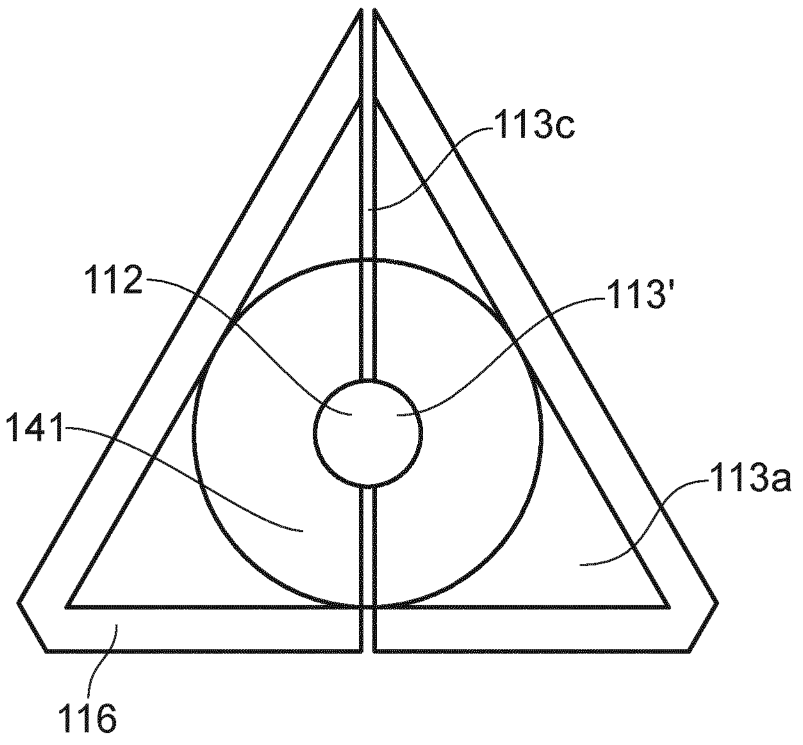
FIGS. 6A and 6B shows a top view and a side view, respectively, of the injection device with a top lid dividable in two parts
Figure 6B:
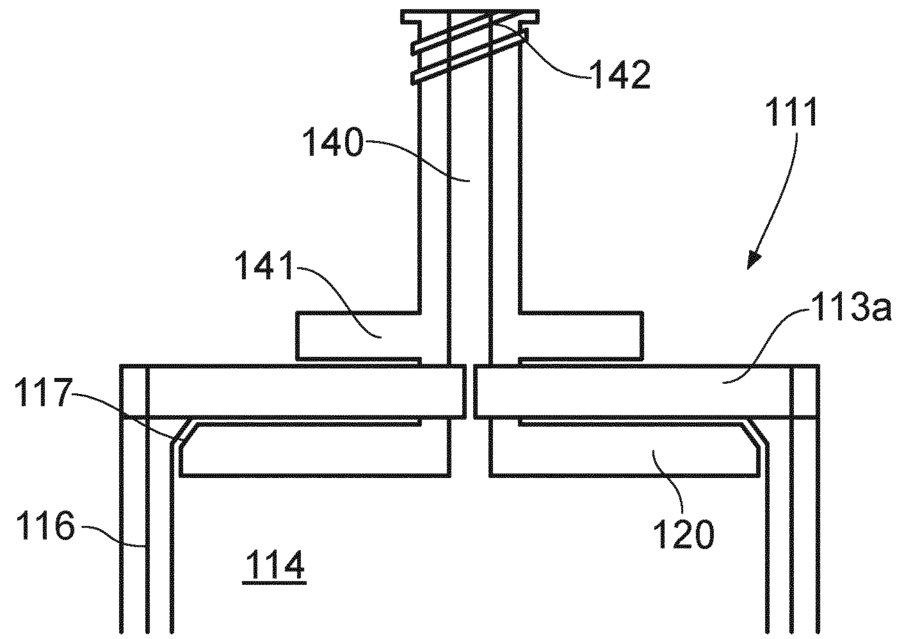

FIGS. 6-7 shows an embodiment of the injection device 100 comprising a top lid 113 that is dividable into 2 parts and a piston 120 that is slidingly and sealably arranged between the side walls 116 within the distribution chamber 114. After being divided the top lid 113 may be removed and the piston 120 may be pushed towards the base end for driving out any remaining injection fluid 150 within the distribution chamber 114.

Figure 8A:
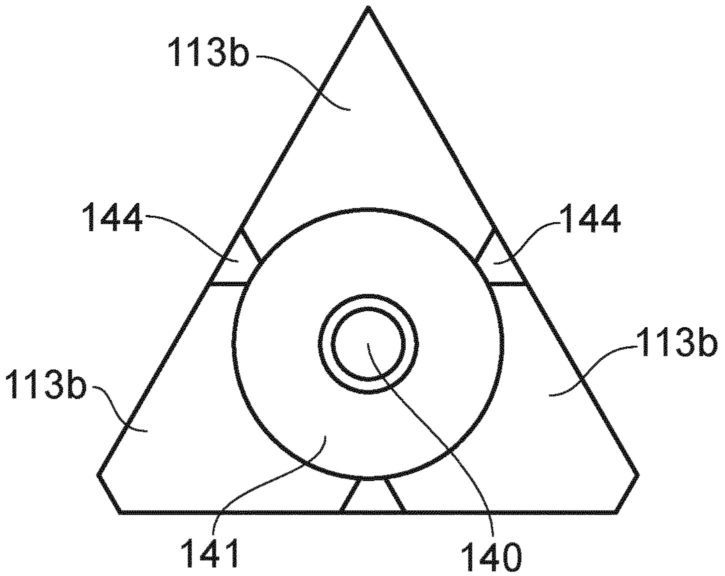
FIGS. 8A and 8B shows a top view of the injection device where top lid is dividable in 3 parts.
Figure 8B:
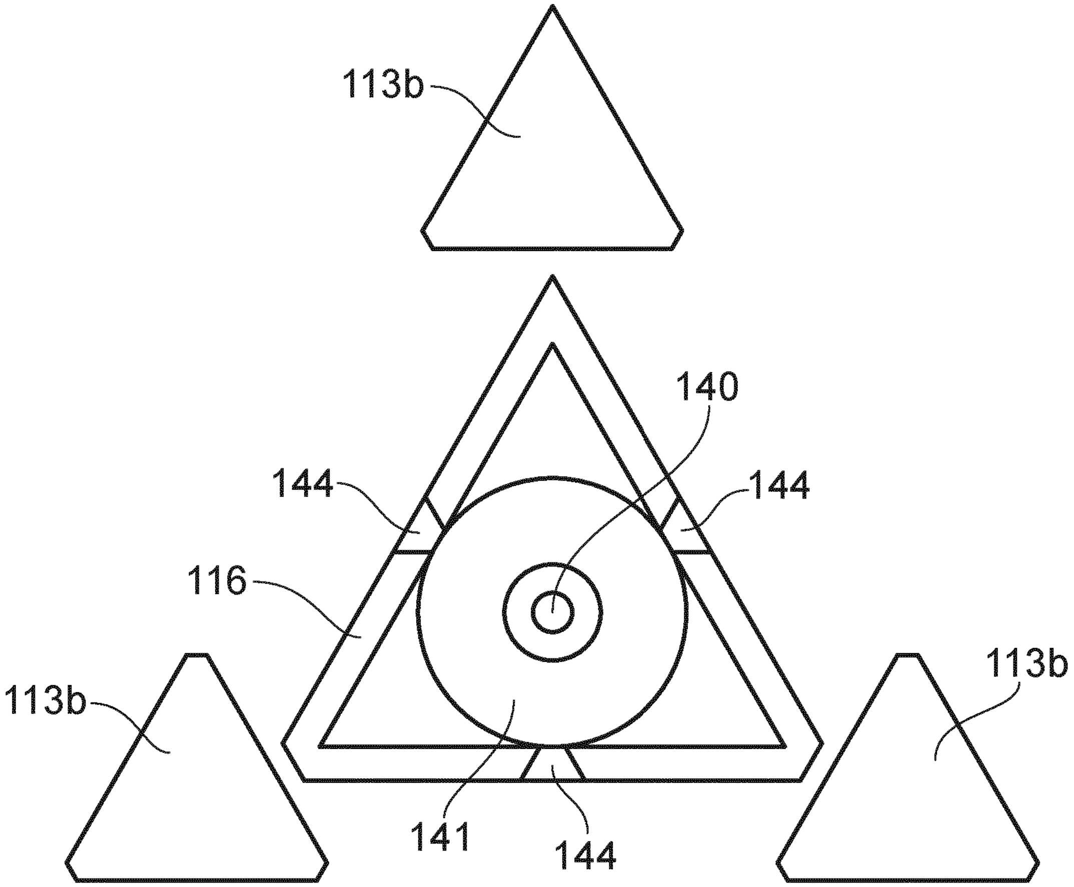
Figure 9:
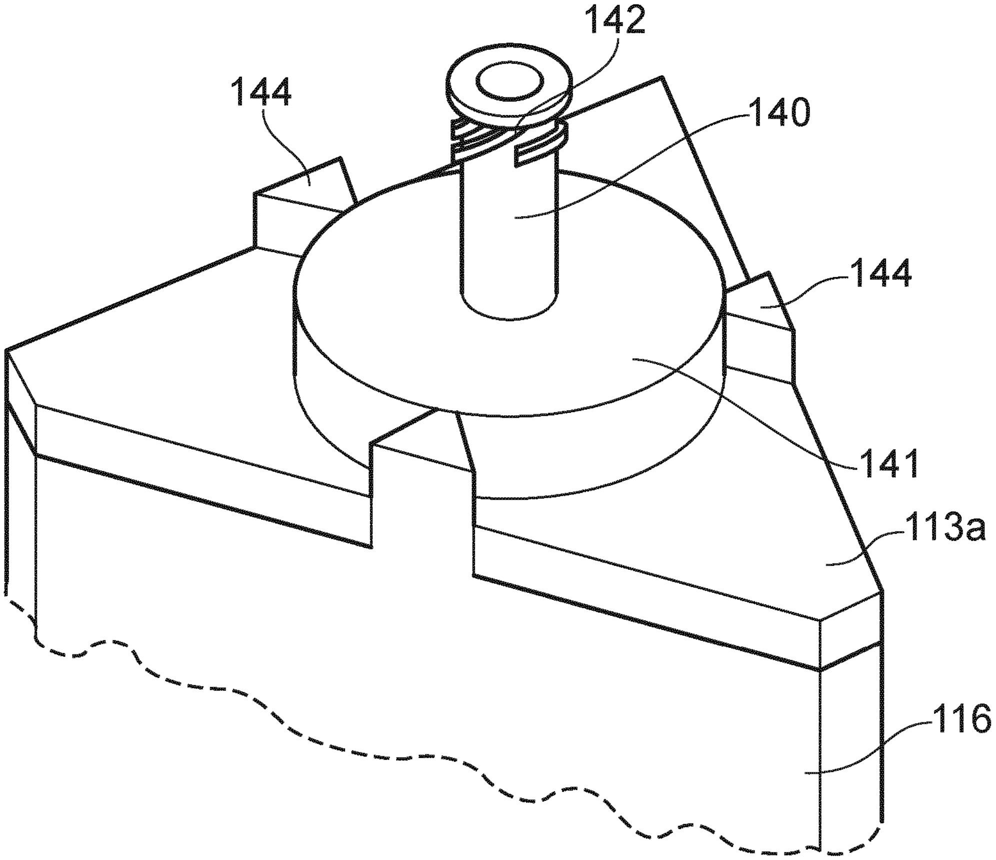
FIG. 9 shows a view from perspective where the top lid is dividable in three parts and there are guiding pins for guiding the stop ring into the distribution chamber shown.

FIGS. 8-9 shows an embodiment wherein the top lid 113 is dividable into 3 parts and the top end comprises 3 guiding pins 144 suitable for engaging with a stop ring 141 on a fluid conduit for guiding the piston 120 into the distribution camber 114.

Figure 10A:
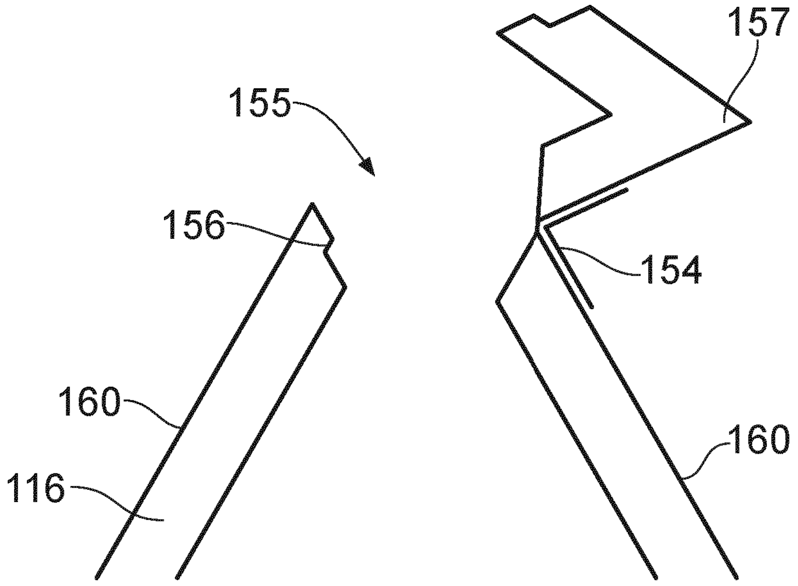
FIGS. 10A and 10B shows a top view of the distribution chamber with a ventilating opening in open position in FIG. 10A and the closed position in FIG. 10B.
Figure 10B:
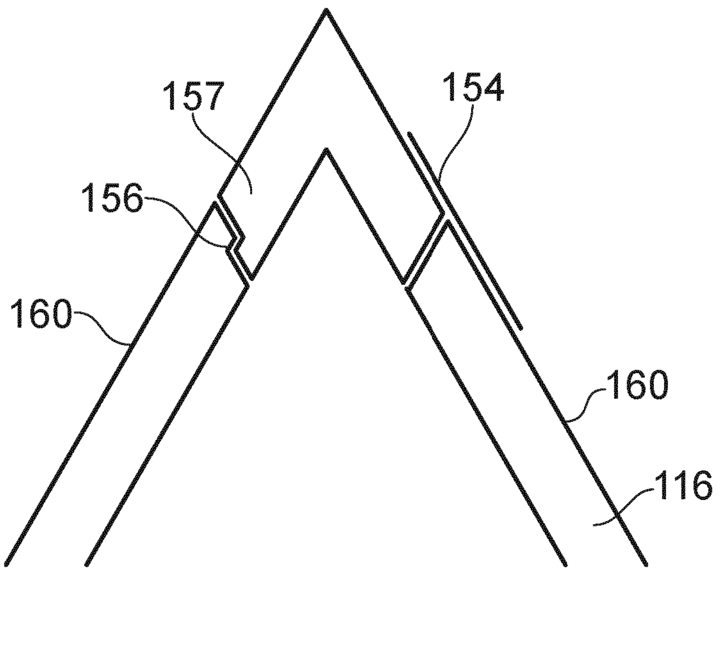

FIGS. 10A, 10B shows an aspect of the injection device 100 with a ventilating opening 155 for evacuating entrapped air in the distribution chamber 116 in a closed position and an open position.

Figure 11:
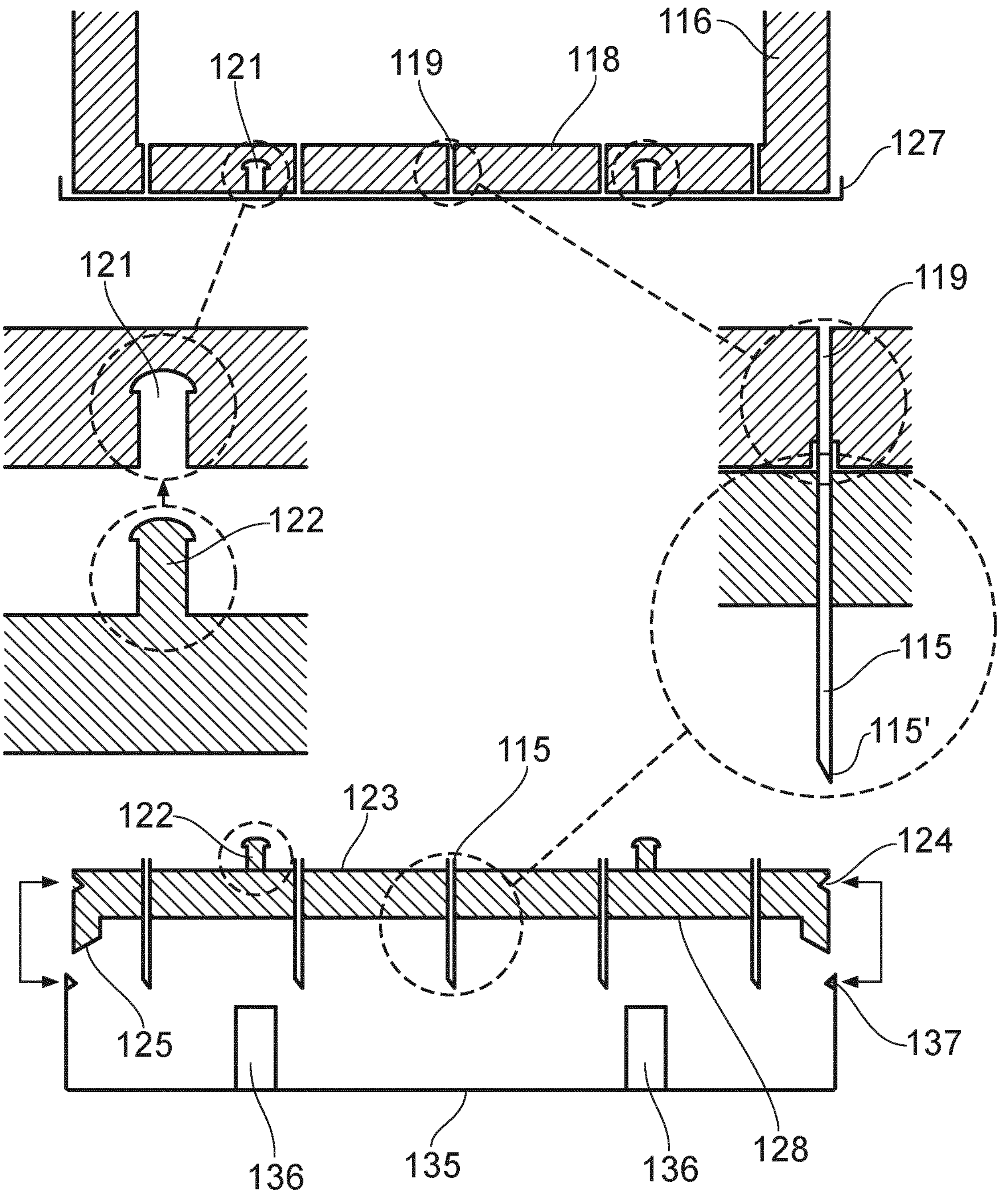
FIG. 11 Shows an exploded view of the assembly of the cannula plate with the base end and the protective cap.

FIG. 11 shows an embodiment of the injection device that has a protective cap where a cannula plate 123 is to be fastened to the base end 118 prior to use. The distribution chamber 114 is typically sealed with a base end protective foil 127 which is removed before the cannula plate 123 is connected to the base end 118.

Figure 12A:
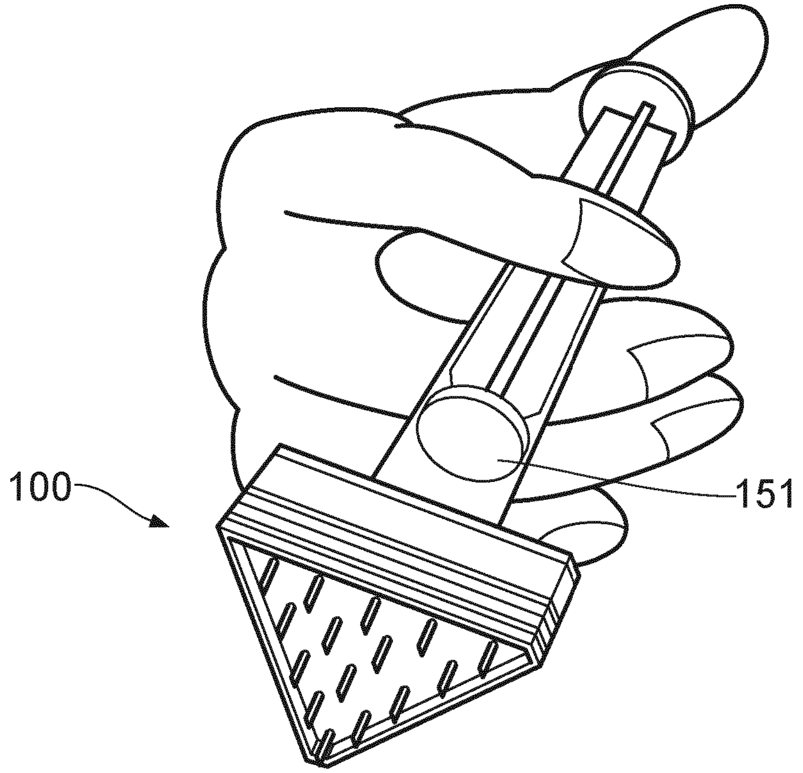
FIGS. 12A and 12B shows the device connected to a syringe, ready for use.
Figure 12B:
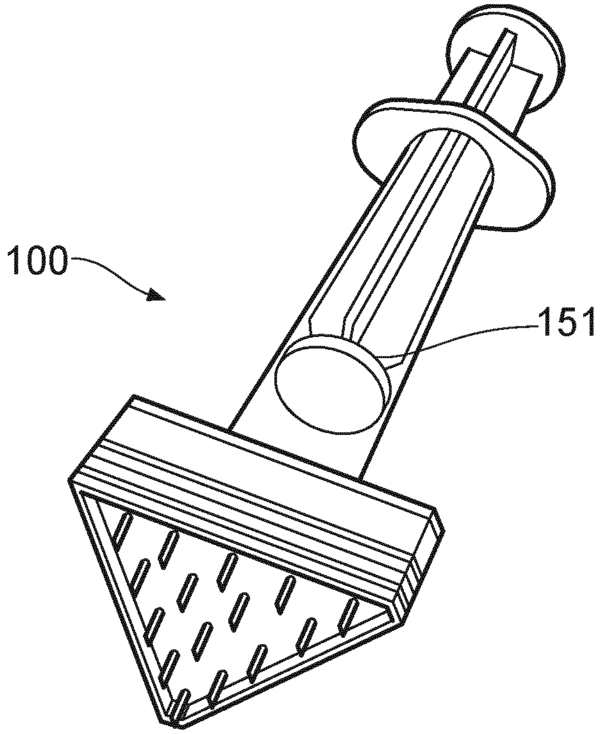
Figure 13:
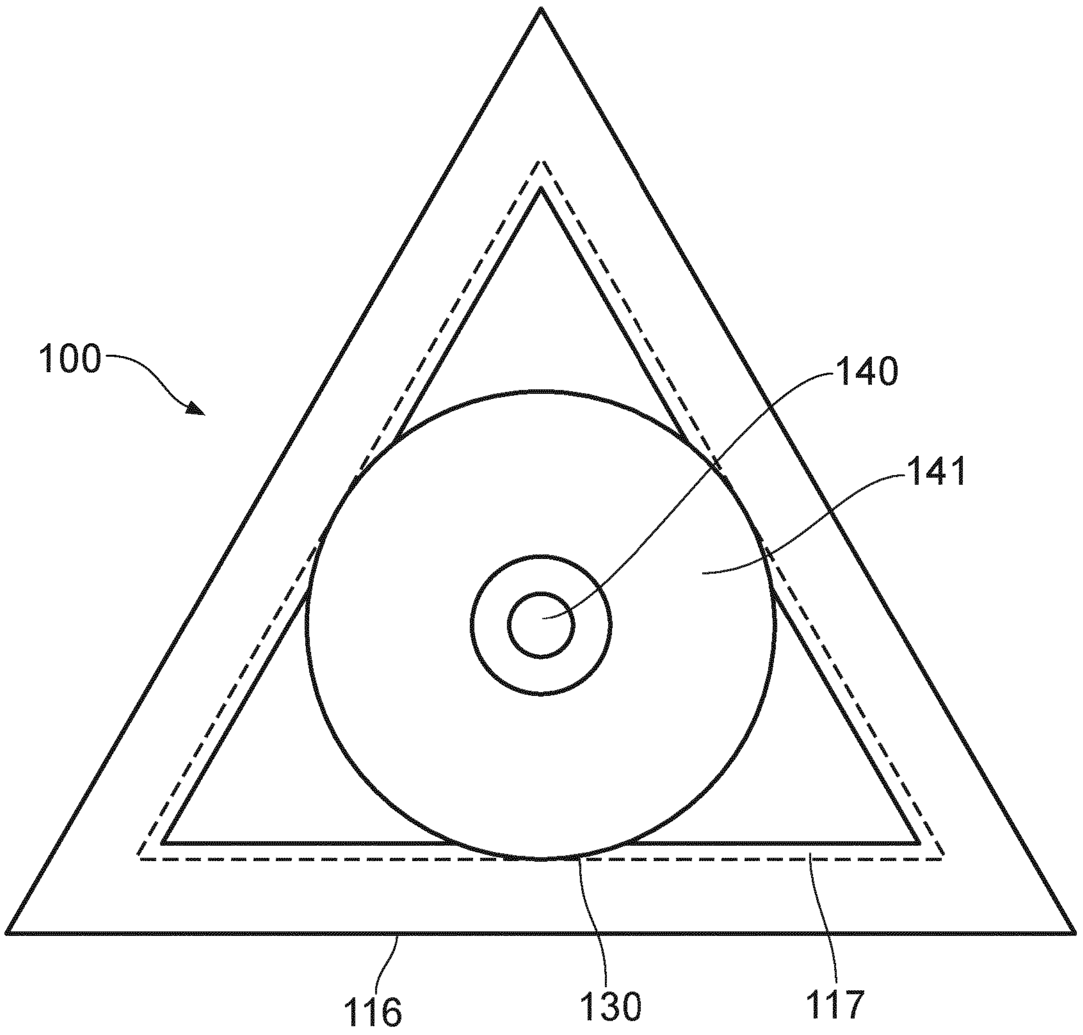
FIG. 13 shows a top view of the device with the stop ring and the stop list recesses

FIGS. 12A and 12B shows a ready to use injection device 100 according to the present invention.

The invention will now be explained in further detail with reference to FIG. 1-12:

The present invention is suitable for use in the treatment of skin and is for use with standard syringes for injections. The present invention comprises an array with a plurality of cannulas that are preferably identical and is configured to provide a plurality of standardized micro injections simultaneously. The present invention advantageously provides injections that are evenly distributed with a predetermined distance between injections and a predetermined depth of injection for each said injection.

In humans the epidermis is about 0.5-1.5 mm thick. Dermis is about 1.5-4 mm thick. The thickness of the layers varies for different parts of the human body, but generally have about the same thickness in everybody within a given age group. Beneath the dermis we find subcutis. Treatment by use of the present invention relates to delivery of injection fluid deep dermally or sub dermally.

The present invention is suitable for treatment of the skin with injection fluids comprising injectable types of substances that include deoxycholic acid, hyaluronic acid, botulinumtoxin, lidocaine, saline, hyaluronic acid filler, Non Animal Stabilized Hyaluronic Acid (NASHA), or calcium hydroxyapatite, poly-1-lactic acid, polyglycolic acid, collagen wrinkle filler, bovine collagen-containing polymethyl methacrylate, autogenous wrinkle filler, but are not limited thereto. The skilled person acknowledges that injectable fluids comprising other active ingredients may also be suitable.

Figure 1:
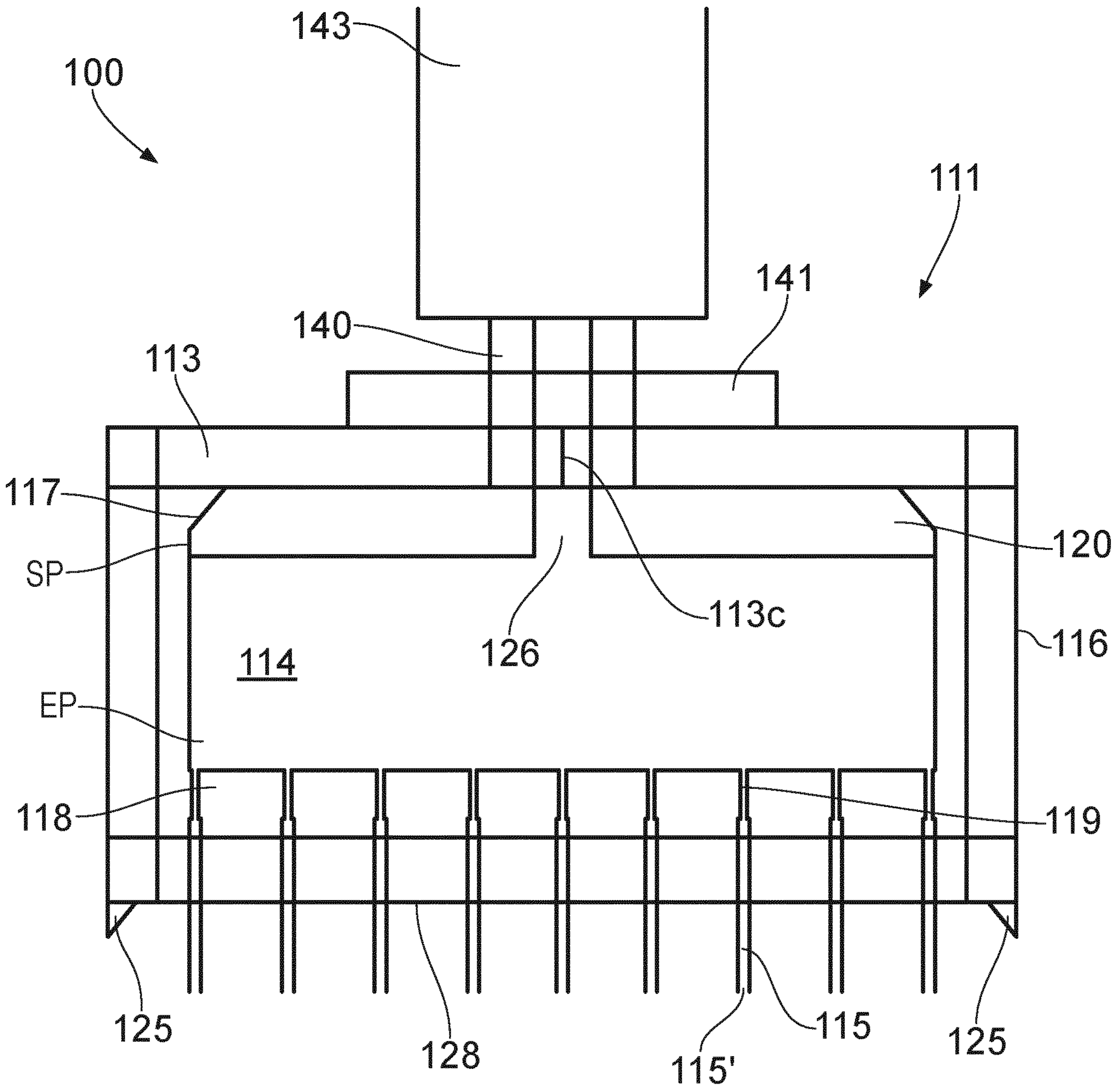
FIG. 1 is a side view of the injection cannula array device. A connected syringe is not shown.

FIG. 1 shows an exemplary embodiment of the injection device 100 according to the present invention, comprising a distribution chamber 114. The distribution chamber 114 is defined by a base end 118, side walls 116 and a top end 111. The base end 118 comprises a plurality of apertures 119 that is in fluid connection with a respective plurality of cannulas 115 with cannula tips 115' for penetrating the skin of a subject.

The outer edge of the base end 118 comprises a skirt 125 that extends from the base end 118 at least a part of the length set up by the cannulas 115. The cannulas are arranged in a triangular pattern with a distance D between each of the cannulas 115. Rows of cannulas 115 located adjacent to the skirt with a distance ½ D×Cos 30° from the outer edge of the skirt 125. The outer edge of the skirt 125 is parallel to the outer side walls 116.

The top end 111 comprises an aperture 126 for fluid connection from the distribution chamber 114 to a fluid conduit 140 that is connected to said top end 111.

As shown in FIG. 1 the top end 111 comprises a piston 120 arranged slidingly within the distribution chamber 114. The piston 120 forms a sealing fit with the side walls 116. The piston comprises an aperture 126 that is connected to the fluid conduit 140 allowing for fluid connection from the distribution chamber 114 to the fluid conduit. The piston 120 and the fluid conduit 140 with the stop ring 141 and the fluid conduit connector 142 is in one piece.

The distribution chamber 114 comprises a stop list 117 which protrudes into the distribution chamber 114, perpendicular from the side walls into the distribution chamber 114 at the end of the side walls 116 distal from the base end 118. The stop list 117 is configured to engage with the piston 120 and prevent it from sliding out of the distribution chamber 114 when the lid 113 has been removed.

The fluid conduit comprises a stop ring 141 that is an annular protrusion extending perpendicular from and fixed to the fluid conduit 140.

The top end 111 further comprises a top lid 113 that is located between the piston 120 and the stop ring 141. The top lid 113 rests on the side walls 116 proximal to the fluid conduit 140. This configuration locks the piston 120 in a starting position (SP) at the stop list 116, wherein the distribution chamber 114 can accept injection fluid 150.

The top lid 113 comprises a top lid aperture 113' for the fluid conduit 140 to pass therethrough.

The fluid conduit 140 comprises a fluid conduit connector 142 located distal to the top end 111. The fluid connector 142 is suitable for connecting the injection device 100 to a syringe 151. The fluid connector 142 is a Luer lock type connector, which is well known. In FIG. 1 the fluid conduit connector 142 is shown with a fluid conduit connector protector 143, which is a Luer lock protector.

The syringe 151 contains the injection fluid 150. When the piston of the syringe 151 is pushed down injection fluid flows through the injection device 100 and out of the cannulas 115.

When the piston of the syringe 151 is pushed until the piston of the syringe 151 reaches the syringe 151 bottom, all injection fluid 150 is purged from the syringe 151 and the flow of injection fluid 150 will stop. A rest volume of injection fluid 150 is trapped within the distribution chamber 114.

The top lid 113 is configured to be removed from the position between the stop ring 141 and the top of the side walls 116. Removal of the top lid 113 makes the piston 120 free to move in the direction of the base end 118.

When the top lid 113 is removed and a force is applied to the piston 120, the piston 120 moves from a starting position (SP) at the stop list 117 to an end position (EP) at the base end 118 and thereby forcing the rest volume of injection fluid 150 out of the distribution chamber 114 through the cannulas 115.

Figure 7A:
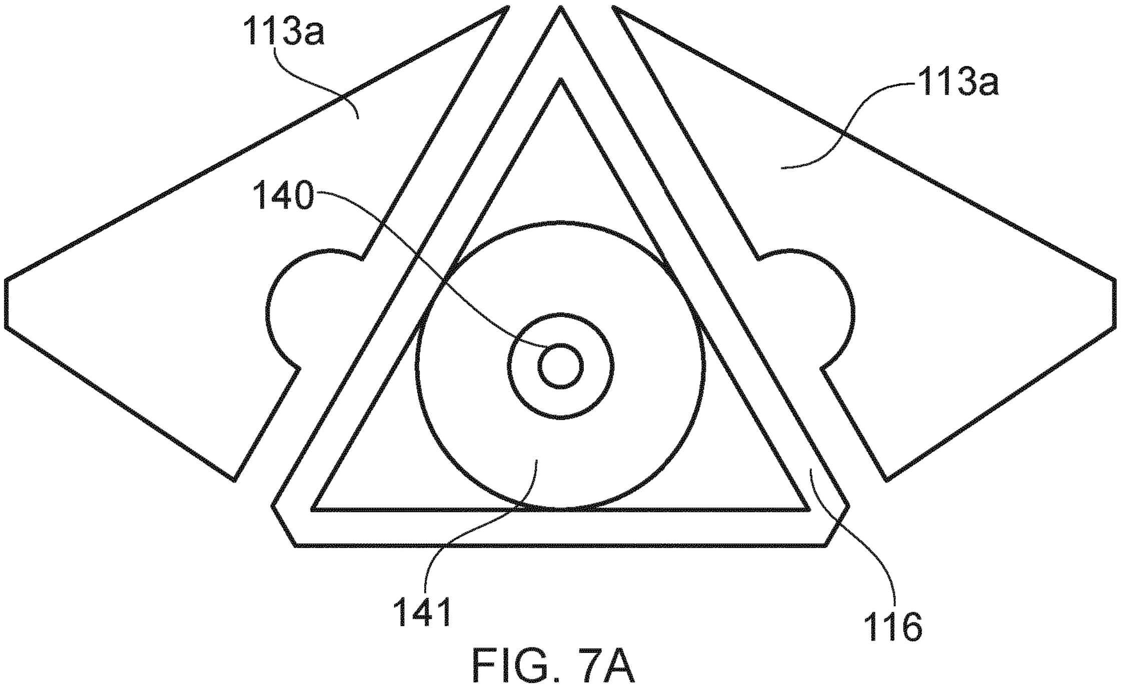
FIG. 7A shows a top view of the injection device where the top lid has been divided in two parts
Figure 7B:
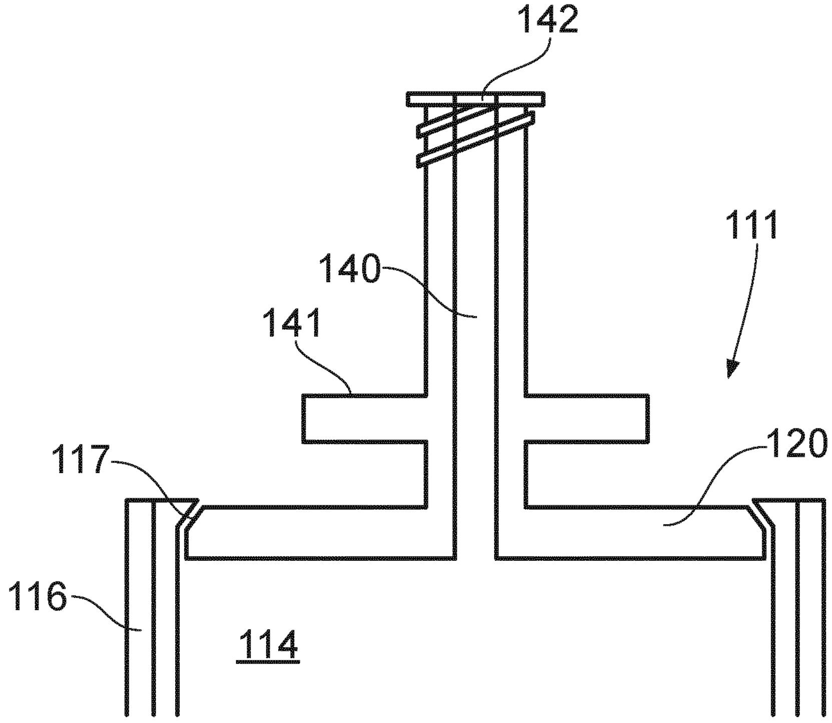
FIG. 7B shows a side view of the injection device where the top lid has been divided in two parts and removed. The piston can be pushed down.

As best shown in FIG. 7A the top lid 113 is in one embodiment configured to be split in two parts **113*a* for removing the top lid 113. FIG. 7B shows the injection device 100 where the top lid 113 is removed and the piston 120 is free to move into the distribution chamber 114**.

FIG. 8A shows another embodiment of the injection device 100 where the top lid 113 is configured to be split into three parts **113*b*. As shown in FIGS. 8A, 8B and 9 the injection device comprises guiding pins 144 protruding from the edge of the top end 111 parallel to the side walls 116. The guiding pins engages with the stop ring 140 for secure guiding the initial movement of the piston 120 into the distribution chamber 114, avoiding any side to side movement and securing vertical movement of the piston 120 into the distribution chamber 114**.

FIGS. 10A and 10B shows an embodiment of the injection device 100 comprising a ventilating opening 155 in an open position and closed position respectively. The distribution chamber 114 comprises a closing mechanism 156 arranged on a hinge 154 for securing a ventilating closure 157. The ventilating opening is located at the corner of the triangular distribution chamber 114 where two long surfaces 160 is connected and allows for evacuating air through the ventilating opening 155 and filling the distribution chamber 114 completely with injection fluid 150. When evacuating air from the distribution chamber 114 the ventilating opening must face up such that any air in the distribution chamber 114 gathers in the corner comprising the ventilating opening 115. The ventilating opening 155 is closed by operating the closing mechanism 156 when the distribution chamber 114 is full of injection fluid 150 and thereby closing the distribution chamber 114 which is now completely filled with injection fluid 150.

As shown in FIG. 11 in one embodiment of the injection device 100 the base end 118 is sealed with a protective foil 127. The injection device 100 is connected to a syringe 151 containing injection fluid 150 and turned so the base end 118 is vertical and the ventilating opening 155 faces up. The distribution chamber 114 is filled completely as air is evacuated and the distribution chamber 114 is then sealed as the ventilating opening 155 is closed. The base end 118 is then turned facing up before the protective foil 127 is removed.

The plurality of cannulas 115 are provided on a separate cannula plate 123. The cannulas 115 are protruding from cannula plate 123 at the opposite side of the cannula tips 115' and align with the base end apertures 119 to provide a fluid connection between the cannula tips 115' and the distribution chamber 114 when the cannula plate 123 is connected to the base end 118. This allows for providing the option of choosing sets of different size of cannulas 115 without needing to replace the entire injection device 100. The base end 118 is configured with female cannula plate connectors 121 for accepting male cannula plate connectors 122 located on the cannula plate 123. When the male cannula connector 122 is clicked in place in the female cannula connector 121 the cannula plate 123 is connected firmly to the base end 118.

FIG. 11 further shows a protective cap 135 comprising a plurality of protective cap spacers 136. The protective cap 135 is fastened on the cannula plate 123 with protective cap connectors 137 which are configured to engage a cannula plate recess 124 for securing the protective cap 135 to the cannula plate 123. The protective cap spacers 136 are a little longer than the cannulas 115 as measured from the cannula plate 123 to the cannula tips 115' thus protecting the sharp, delicate cannula tips 115' from damage as well as protecting a user from unintentional stings from cannulas 115 prior to use of the device. The cannula tips 115' cannot contact the protective cap 135, when the protective cap 135 is connected to the cannula plate 123.

As shown in FIGS. 2, 9 12A and 12B the outer relief of the skirt 125 and the outer relief of the side walls 116 is configured with a diamond shape. The shape is substantially triangular comprising two connected long surfaces 160, wherein each of the two connected long surface 160 is connected to two respective corner surfaces 161 at the respective ends distal to the connection between the two long surfaces 160 and one short surface 162 connected at each end to the respective corner surfaces 161. The corner surface 161 is ½ D long, and has an inner angle of 120° towards the two adjacent surfaces.

The injection device comprises a cannula array surface 128 at the base end of the cannulas 115. The cannula array surface 128 is flat. This allows for exact injection depth to be decided prior to the treatment by the practitioner since the cannulas 115 will not penetrate the skin any deeper than the length of the cannulas' 115 protrusion from the cannula array surface 128 The flat surface of the cannula array 128 effectively stops the cannulas' 115 penetration when the flat cannula array surface 128 is pressed against the skin of a person being treated.

Figure 2:
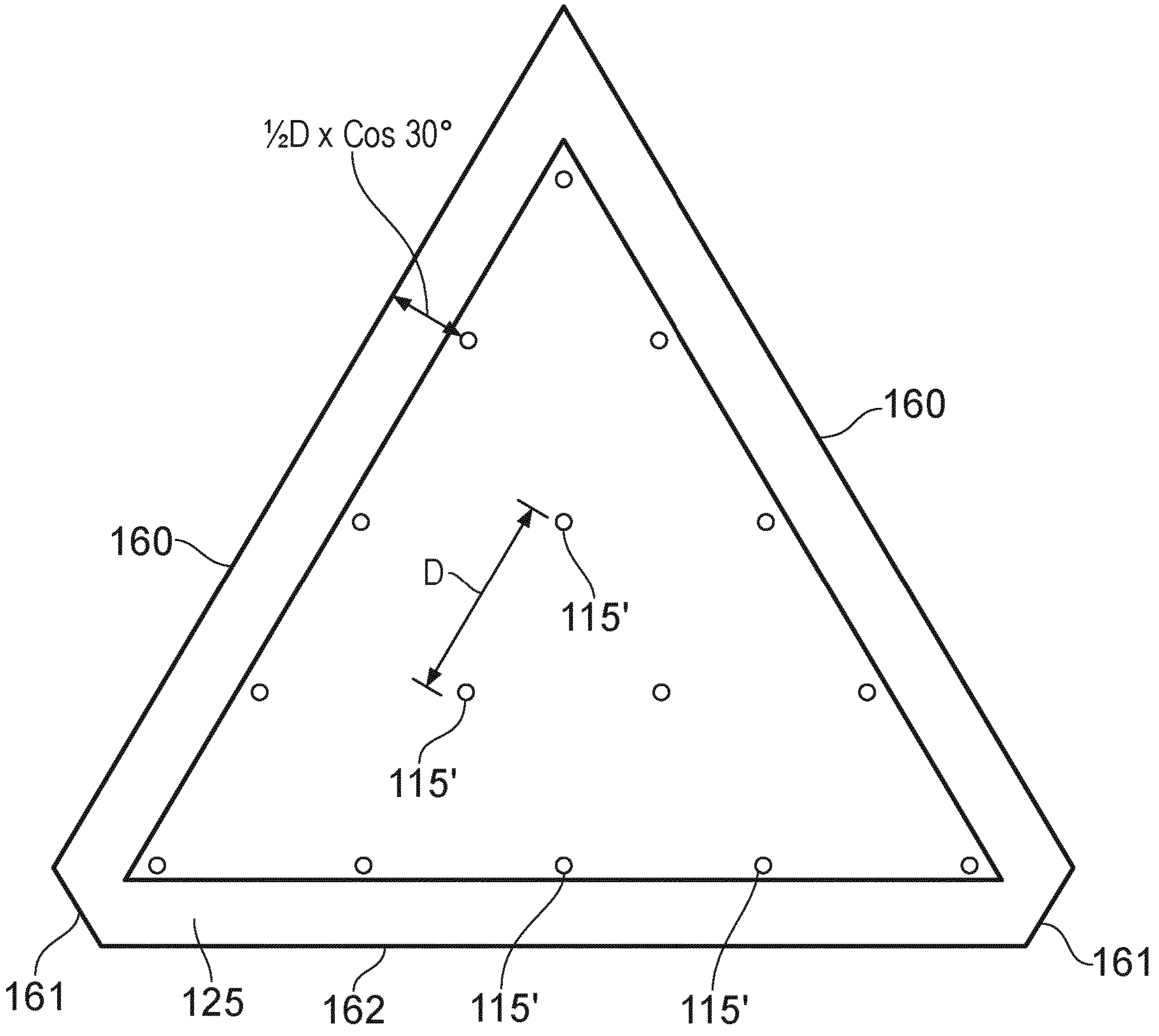
FIG. 2 is bottom view of the device, showing the skirt and the cannula tips arranged with a distance D between them, and also showing that the distance from a cannula adjacent to the skirt to the outer edge of the skirt is ½ D×Cos 30°.

As shown in FIG. 2 the cannulas 115 are arranged with a distance D between each cannula 115. The cannulas 115 adjacent to the skirt 125 are located a distance ½ D×Cos 30° from the outer edge of the skirt 125. The outer edge of the skirt 125 is configured to leave a temporary visible line in the patients skin after an injection to a patient, where the injection device is pressed against the patients skin in order to achieve penetration of all the cannulas 125 into the desired depth of the patients skin. The temporary line in the patient's skin can advantageously be used as a means for lining up the next injection. By moving and placing the skirt 125 of the injection device adjacent to the temporary line a second injection is given while sustaining the distance D between all injection points by cannulas 125. This is due to that the cannulas 115 adjacent to the skirt 125 are located a distance ½ D×Cos 30° from the closest outer edge of the skirt 125, when measured at an angle perpendicular to the closest outer edge of the skirt 125. Placing the skirt 125 directly adjacent to the temporary line in a patient's skin will yield a distance ½ D+½ D=D between adjacent injection points. This is given, since the cannulas 115 adjacent to the skirt 125 of two adjacent injection points forms patterns of equilateral triangles where the sides measures D when two adjacent administrations are aligned as shown in FIGS. 3A-3C.

The distance D may vary according to the needs of the specific skin treatment to be given.

The skin area to be treated can be expanded by administering multiple injections to a patient. Each time aligning the injection device 100 by using the temporary line left in the patient's skin by the skirt 125 which have been pressed onto the skin.

Figure 3A:
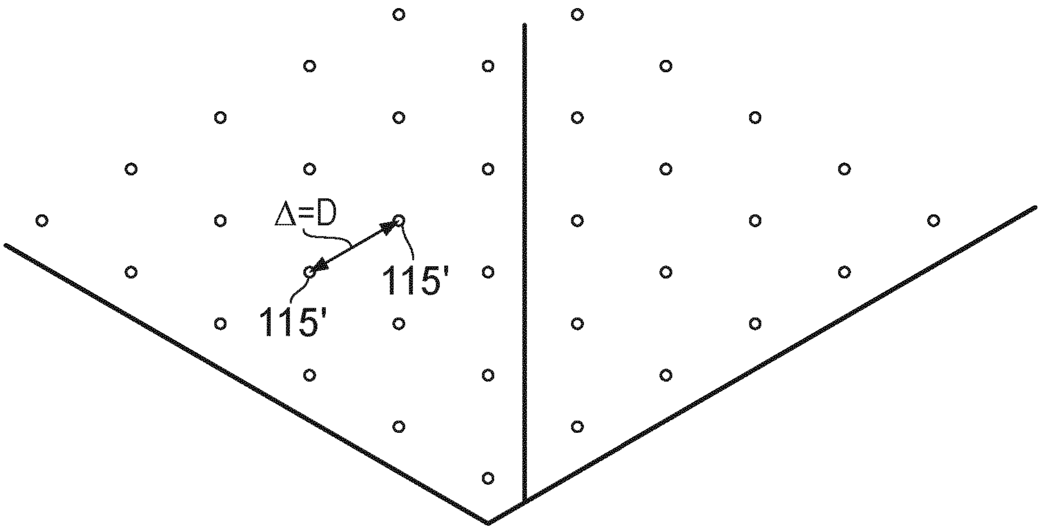
FIG. 3A-3C shows different options for patterns of injection points for the cannulas when a practitioner administers doses using the skirt for lining up all injections at a distance D between injections.
Figure 3B:
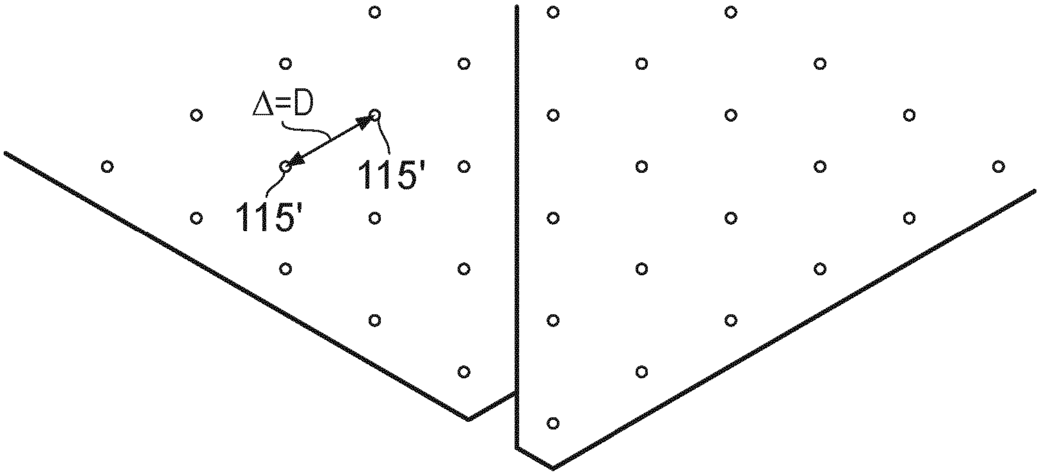
Figure 3C:
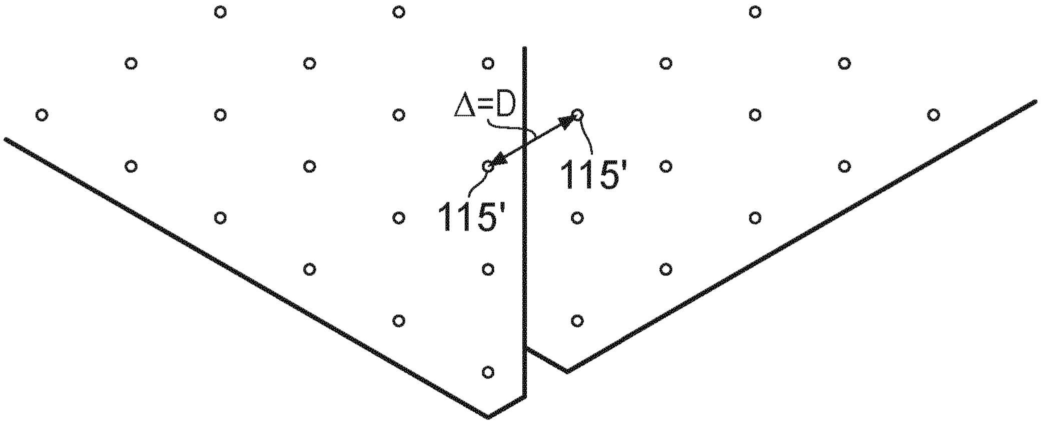
Figure 4A:
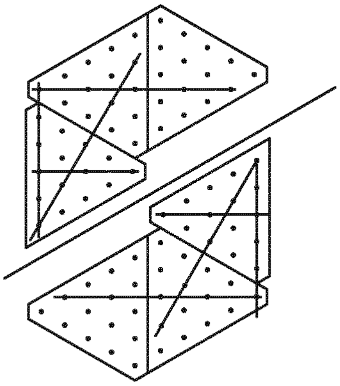
FIG. 4A-4F shows some different possibilities for expanding patterns of injections where the distance is D between injections.
Figure 4C:
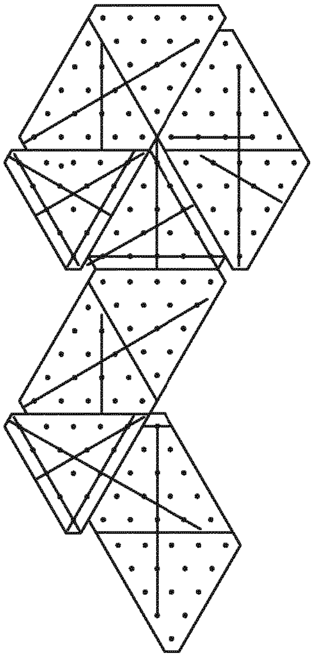
Figure 4D:
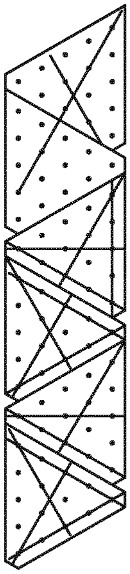
Figure 4B:
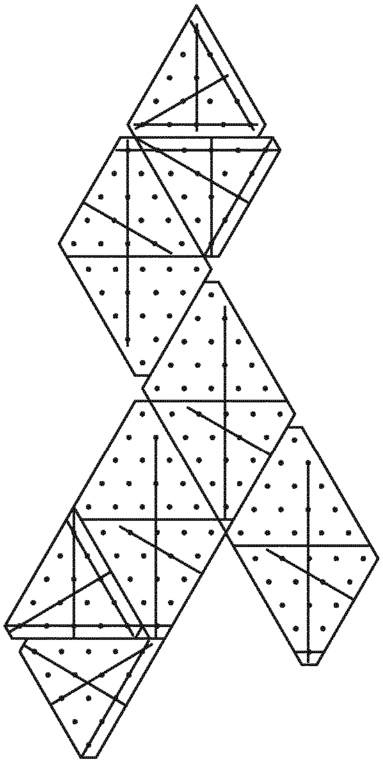
Figure 4F:
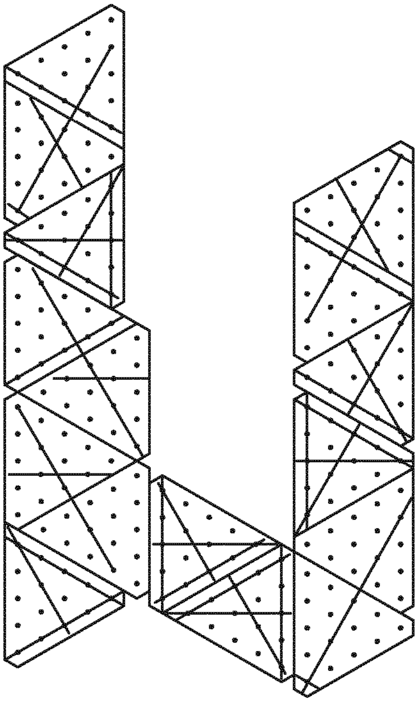
Figure 4E:
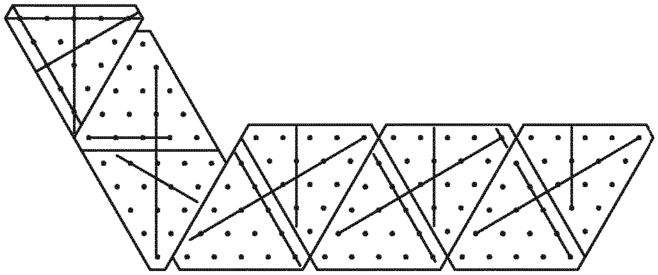
Figure 5A:
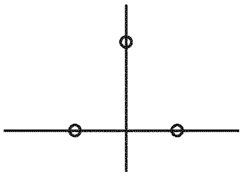
FIG. 5A-5E shows some possible number of cannulas of one injection device.
Figure 5B:
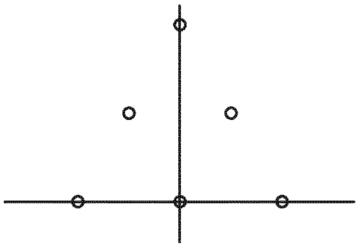
Figure 5C:
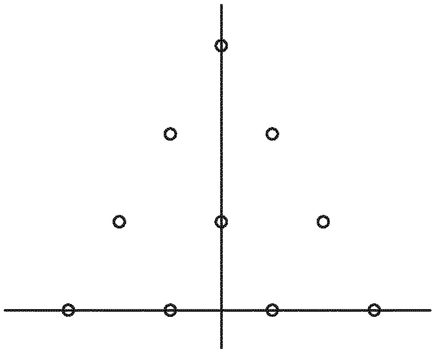
Figure 5D:
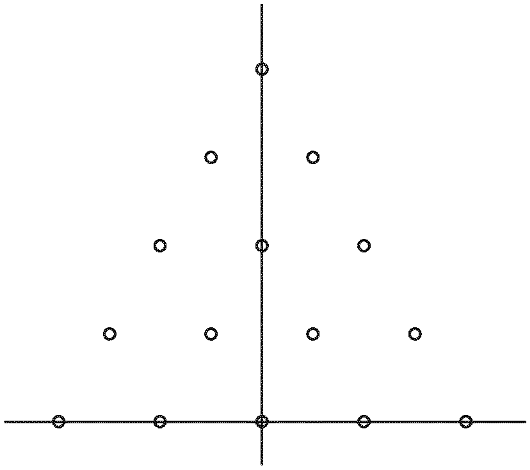
Figure 5E:
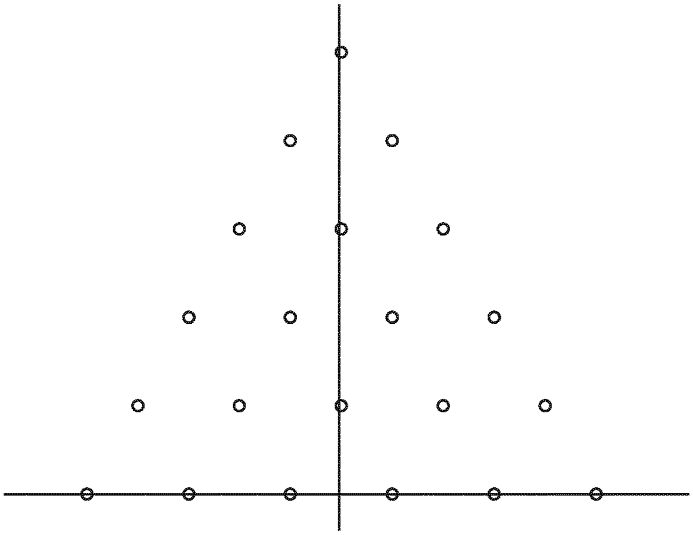

FIGS. 3A-3C shows how the administrations can be aligned to secure even and uniform distribution by keeping the distance between each injection site of a cannula at a distance D. The diamond shape with the corner surfaces 161 will be of help. When a new administration is to be applied the injection device may be rotated in 3 different ways.

- The pointed corner where the two long surfaces 160 are connected are aligned with where the short side 161 and the corner side 162 are connected, as shown in FIG. 3A
- When administration is given with short sides 161 adjacent to each other, the new administration is aligned at the extension line of a long side 160 from the prior administration. There are two possible ways to do this as shown in FIGS. 3B and 3C.

FIGS. 4A-4F shows examples of how the administration of active ingredient can be expanded to larger areas of skin in a patient while keeping the even and uniform distance D between each injection point by each cannula 115.

FIG. 5A-5E shows that the number of cannulas 115 can be scaled to the needs of a specific treatment. This also allows for scaling the size of the area that is to be treated. As shown in FIG. 5A-5E the device may comprise for example 3, 6, 10, 15 or 21 cannulas, but a skilled person would acknowledge that this is not meant to be limiting and that the injection device may comprise 28, 37, etc cannulas 115 arranged in the shown triangular shape.

The injection device 100 is therefore suitable for administering an injection fluid 150 evenly and uniform to an area of skin by providing triangular shaped patterns of injection sites as shown in FIGS. 3-5.

In one embodiment the invention relates to a method for obtaining even distribution of an injection fluid 150 by use of the injection cannula array device 100 according to claim, comprising the steps of A. connecting the injection cannula array device 100 to a syringe 151 comprising injection fluid 150

B. inserting the needles into the skin of a patient and contacting the skin of a patient with the skirt 125 by pressing the device 100 against the skin of the patient with sufficient force for the skirt 125 to leave a temporary line in the shape of the skirt 125 on the skin surface of the patient, C. delivering a predetermined volume of injection fluid 150 from the syringe 151, D. removing the injection cannula array device 100, E. spotting the temporary line in the skin surface of the patient, F. moving the injection cannula array device 100 and aligning an outer surface of the skirt 125 to the temporary line on the skin surface of the patient, G. optionally repeating step A The method can further relate to by use of the injection cannula array device 100, wherein the method further comprises the steps of H. removing the top lid 113

I. applying a force to the fluid conduit 140 for pushing the piston 120 to the base end 113, thereby emptying the distribution chamber 114.

It is appreciated that certain features of the invention, which, for clarity, have been described above in the context of separate embodiments, may also be provided in combination in a single embodiment. Conversely, various features of the invention, which, for brevity, have been described in the context of a single embodiment, may also be provided separately or in any suitable sub-combination.

Table of references:

| | |
|---|---|
| 100 | Injection device |
| 111 | Top end |
| 113 | Top lid |
| 113' | Top lid aperture |
| 113a | Top lid part |
| 113b | Top lid part |
| 113c | Top lid dividing line |
| 114 | Distribution chamber |
| 115 | Cannula |
| 115' | Cannula tip |
| 116 | Side wall |
| 117 | Stop list |
| 118 | Base end |
| 119 | Base end aperture |
| 120 | Piston |
| 121 | Female cannula plate connector |
| 122 | Male cannula plate connector |
| 123 | Cannula plate |
| 124 | Cannula plate recess |
| 125 | Skirt |
| 126 | Aperture |
| 127 | Base end protective foil |
| 128 | Cannula array surface |
| 130 | Stop list recess |
| 135 | Protective cap |
| 136 | Protective cap spacer |
| 137 | Protective cap connector |
| 140 | Fluid conduit |
| 141 | Stop ring |
| 142 | Fluid conduit connector |
| 143 | Fluid conduit connector protector |
| 144 | Guiding pins |
| 150 | Injection fluid |
| 151 | Syringe |
| 154 | Hinge |
| 155 | Ventilating opening |
| 156 | Ventilating opening closing mechanism |
| 157 | Ventilating opening closure |
| 160 | Long surface |
| 161 | Corner surface |
| 162 | Short surface |

The invention claimed is:

1. An injection cannula array device comprising:

a fluid conduit comprising a fluid conduit connector suitable for connecting to a syringe;

a distribution chamber comprising:

a top end comprising a top end aperture for fluid communication from the distribution chamber to outside of the distribution chamber, the top end connected to the fluid conduit for fluid communication through the top end aperture;

a base end comprising:

base end apertures for fluid communication from the distribution chamber to the outside of the distribution chamber; and a skirt extending from an outer edge of the base end, the skirt suitable for leaving a distinct guiding mark on a skin surface after the skirt has been pressed against the skin surface; and side walls connected to the base end;

a piston slidingly and sealably arranged between the side walls within the distribution chamber, the piston connected to the fluid conduit and comprising a piston aperture for fluid communication from the distribution chamber through the fluid conduit, the piston configured:

with a start position at the top end of the distribution chamber;

with an end position at the base end of the distribution chamber; and to travel from the start position towards the end position when a predetermined force is applied to the fluid conduit in a direction towards the base end of the distribution chamber; and cannulas arranged in rows, each cannula:

arranged for fluid communication with a respective base end aperture of the base end apertures;

extending from the respective base end aperture to a cannula tip distal from the base end outside the distribution chamber; and separated from one or more adjacent cannulas by a distance D;

wherein:

the skirt extends between 5-90% of a length of the cannulas; and a distance from each cannula located adjacent to the skirt to the outer edge is between $\frac{1}{2}D\times\cos 25°$-$\frac{1}{2}D\times\cos 35°$, when measured at angle perpendicular to the skirt.

2. The injection cannula array device according to claim 1, wherein the distribution chamber has an inner shape of an equilateral triangle in a plane of the base end.

3. The injection cannula array device according to claim 1, wherein:

the skirt comprises outer walls; and the outer walls of the skirt comprise:

two connected long surfaces;

two corner surfaces; and one short surface longer than each of the two corner surfaces;

each long surface being longer than the short surface and being connected to a respective corner surface of the two corner surfaces at an end distal to the connection between the two connected long surfaces; and the short surface being connected at each end to each respective corner surface.

4. The injection cannula array device according to claim 1, wherein:

the side walls of the distribution chamber comprise a stop list protruding from the side walls proximal to the top end, into the distribution chamber; and the stop list is configured to engage with the piston, at the start position, thereby hindering travel of the piston out of the distribution chamber.

5. The injection cannula array device according to claim 1, wherein the top end of the distribution chamber further comprises:

a top lid comprising a top lid aperture for enclosing the fluid conduit, the top lid arranged for covering the side walls and the piston, and the top lid configured to be separated into at least two parts along a line traversing the top lid aperture.

6. The injection cannula array device according to claim 5, wherein the top lid is configured to be separated into three parts.

7. The injection cannula array device according to claim 5 or claim 6, wherein the fluid conduit further comprises:

a stop ring protruding from an outside of the fluid conduit, the stop ring arranged to engage the top lid, thereby preventing movement of the fluid conduit and securing the piston in the start position when the top lid is covering the side walls and the piston.

8. The injection cannula array device according to claim 7, wherein:

the stop ring has a diameter suitable for a tight fit with the side walls when the piston travels from the start position towards the end position;

the side walls comprise a stop list protruding from the side walls proximal to the top end, into the distribution chamber; and the stop list is configured:

to engage with the piston, at the start position, thereby hindering travel of the piston out of the distribution chamber; and with recesses for allowing the stop ring to pass by and into the distribution chamber.

9. The injection cannula array device according to claim 8, wherein the top end of the distribution chamber further comprises guiding pins for guiding the stop ring into the distribution chamber.

10. The injection cannula array device according to claim 5, wherein the distribution chamber further comprises a ventilating opening for evacuating air from the distribution chamber prior to injecting a patient.

11. A method for obtaining even distribution of an injection fluid by use of the injection cannula array device according to claim 1 comprising:

connecting the injection cannula array device to a syringe containing injection fluid;

inserting the cannulas into the skin of a patient and contacting the skin of the patient with the skirt by pressing the injection cannula array device against the skin of the patient with sufficient force for the skirt to leave a temporary line in a shape of the skirt on the skin surface of the patient;

delivering a predetermined volume of injection fluid from the syringe;

removing the injection cannula array device;

spotting the temporary line in the skin surface of the patient; and moving the injection cannula array device and aligning an outer surface of the skirt to the temporary line on the skin surface of the patient; and optionally repeating the connecting the injection cannula array device to a syringe containing injection fluid.

12. An injection cannula array device comprising:

a fluid conduit comprising a fluid conduit connector suitable for connecting to a syringe;

a distribution chamber comprising:

a top end comprising a top end aperture for fluid communication from the distribution chamber to outside of the distribution chamber, the top end connected to the fluid conduit for fluid communication through the top end aperture;

a base end comprising:

base end apertures for fluid communication from the distribution chamber to the outside of the distribution chamber; and a skirt comprising outer walls and extending from an outer edge of the base end, the skirt suitable for leaving a distinct guiding mark on a skin surface after the skirt has been pressed against the skin surface; and side walls connected to the base end;

a piston slidingly and sealably arranged between the side walls within the distribution chamber, the piston connected to the fluid conduit and comprising a piston aperture for fluid communication from the distribution chamber through the fluid conduit, the piston configured:

with a start position at the top end of the distribution chamber;

with an end position at the base end of the distribution chamber; and to travel from the start position towards the end position when a predetermined force is applied to the fluid conduit in a direction towards the base end of the distribution chamber; and cannulas arranged in rows, each cannula:

arranged for fluid communication with a respective base end aperture of the base end apertures;

extending from the respective base end aperture to a cannula tip distal from the base end outside the distribution chamber; and separated from one or more adjacent cannulas by a distance D;

wherein:

the outer walls of the skirt include two long surfaces, two corner surfaces, and one short surface longer than each of the two corner surfaces, each long surface being longer than the short surface and being connected to a respective corner surface of the two corner surfaces at an end distal to a connection between the two long surfaces, and the short surface being connected at each end to each respective corner surface;

the skirt extends between 10-80% of a length of the cannulas; and a distance from each cannula located adjacent to the skirt to the outer edge is between ½D×Cos 29°-½D×Cos 31°, when measured at angle perpendicular to the skirt.

13. An injection cannula array device comprising:

a fluid conduit comprising:

a fluid conduit connector suitable for connecting to a syringe; and a stop ring protruding from an outside of the fluid conduit;

a distribution chamber comprising:

a top end comprising:

a top end aperture for fluid communication from the distribution chamber to outside of the distribution chamber, the top end connected to the fluid conduit for fluid communication through the top end aperture; and a top lid comprising a top lid aperture for enclosing the fluid conduit, the top lid configured to be separated into at least two parts along a line traversing the top lid aperture;

a base end comprising:

base end apertures for fluid communication from the distribution chamber to the outside of the distribution chamber; and a skirt extending from an outer edge of the base end, the skirt suitable for leaving a distinct guiding mark on a skin surface after the skirt has been pressed against the skin surface; and side walls connected to the base end, the side walls comprising a stop list protruding from the side walls proximal to the top end, into the distribution chamber;

a piston slidingly and sealably arranged between the side walls within the distribution chamber, the piston connected to the fluid conduit and comprising a piston aperture for fluid communication from the distribution chamber through the fluid conduit, the piston configured:

with a start position at the top end of the distribution chamber;

with an end position at the base end of the distribution chamber; and to travel from the start position towards the end position when a predetermined force is applied to the fluid conduit in a direction towards the base end of the distribution chamber; and cannulas arranged in rows, each cannula:

arranged for fluid communication with a respective base end aperture of the base end apertures;

extending from the respective base end aperture to a cannula tip distal from the base end outside the distribution chamber; and separated from one or more adjacent cannulas by a distance D;

wherein:

the top lid is arranged for covering the side walls and the piston;

the stop ring is arranged to engage the top lid, thereby preventing movement of the fluid conduit and securing the piston in the start position when the top lid is covering the side walls and the piston;

the stop ring has a diameter suitable for a tight fit with the side walls when the piston travels from the start position towards the end position;

the stop list is configured to engage with the piston, at the start position, thereby hindering travel of the piston out of the distribution chamber;

the stop list is further configured with recesses for allowing the stop ring to pass by and into the distribution chamber;

the skirt extends between 10-70% of a length of the cannulas; and a distance from each cannula located adjacent to the skirt to the outer edge is ½D×Cos 30°, when measured at angle perpendicular to the skirt.

14. The injection cannula array device according to claim 13, wherein the top end of the distribution chamber further comprises guiding pins for guiding the stop ring into the distribution chamber.

* * * * *